(12) United States Patent
Yasukawa et al.

(10) Patent No.: US 6,491,936 B1
(45) Date of Patent: Dec. 10, 2002

(54) CREAMS CONTAINING VITAMIN $D_3$ DERIVATIVES

(75) Inventors: Satoshi Yasukawa, Tokyo (JP); Takashi Uchio, Tokyo (JP); Keiko Sano, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/162,109

(22) Filed: Jun. 5, 2002

Related U.S. Application Data

(63) Continuation of application No. 09/555,814, filed as application No. PCT/JP98/05536 on Dec. 8, 1998, now Pat. No. 6,432,422.

(30) Foreign Application Priority Data

Dec. 9, 1997 (JP) .............................................. 9-338810
Dec. 9, 1997 (JP) .............................................. 9-338812

(51) Int. Cl.$^7$ .......................... A61K 7/00; A61K 31/59; A61K 31/56; A61K 7/48

(52) U.S. Cl. ........................ 424/401; 514/167; 514/169; 514/182; 514/168; 424/78.03

(58) Field of Search ............................. 424/401, 78.03; 514/167, 169, 182, 168

(56) References Cited

U.S. PATENT DOCUMENTS

| | | | |
|---|---|---|---|
| 4,836,957 A | 6/1989 | Nemoto et al. | |
| 4,871,723 A | 10/1989 | Makino et al. | |
| 5,362,719 A | 11/1994 | Godfredsen | |

FOREIGN PATENT DOCUMENTS

| | | |
|---|---|---|
| JP | 5504959 | 7/1993 |

*Primary Examiner*—Alton Pryor
(74) *Attorney, Agent, or Firm*—Browdy and Neimark

(57) ABSTRACT

The present invention aims to provide an O/W type creams showing improved skin absorption and heat stability of maxacalcitol as an active ingredient. The present invention provides O/W type creams containing maxacalcitol in the oil phase and/or water phase, more specifically O/W creams containing maxacalcitol and an emulsifier wherein maxacalcitol exists in the oil phase as well as O/W creams wherein maxacalcitol exists in the water phase.

7 Claims, 1 Drawing Sheet

F I G. 1
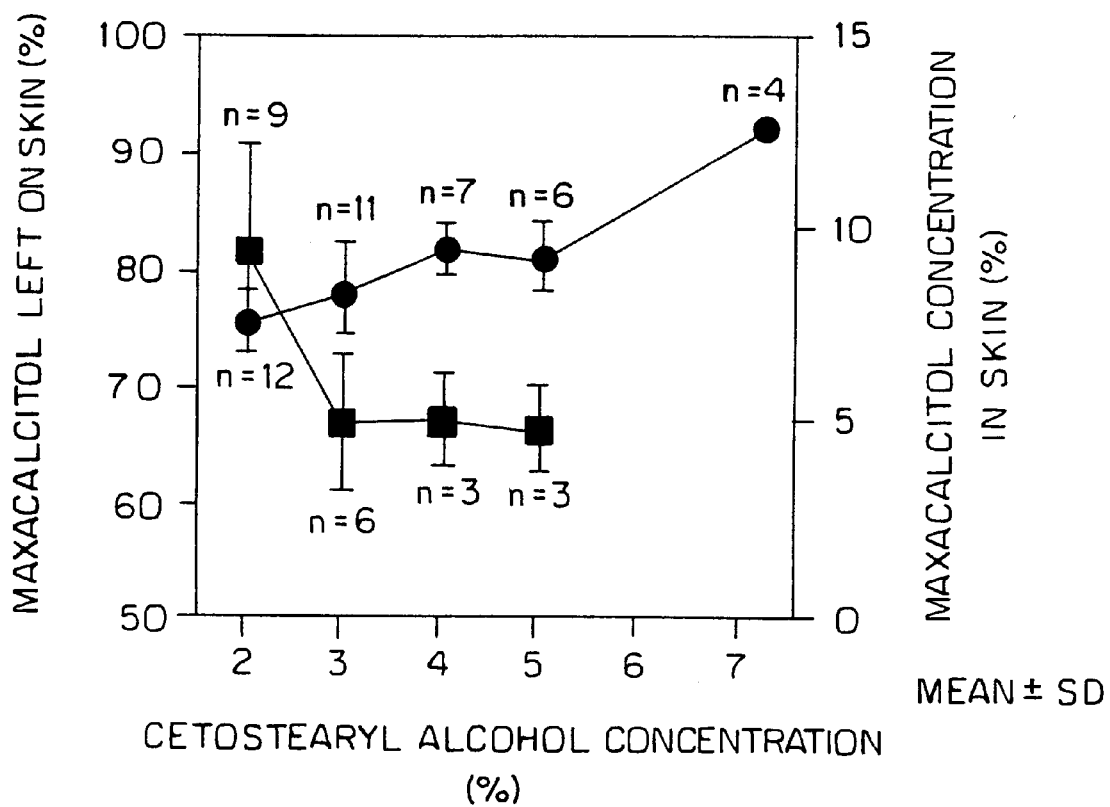

CREAMS CONTAINING VITAMIN D₃ DERIVATIVES

CROSS-REFERENCE TO RELATED APPLICATIONS

The present application is a continuation of application Ser. No. 09/555,814, filed Jun. 5, 2000 now U.S. Pat. No. 6,432,422 which is the national stage under 35 U.S.C. 371 of PCT/JP98/05536, filed Dec. 8, 1998.

FIELD OF THE INVENTION

The present invention relates to O/W type creams for skin application, which creams exhibit improved skin transfer and physical/chemical stability of maxacalcitol as an active ingredient, more specifically, the present invention relates to O/W type creams in which maxacalcitol as an active ingredient exists in the oil phase and/or water phase.

BACKGROUND ART

Some classes of vitamin $D_3$ derivatives such as 1α, 3β-dihydroxy-20α-(3-hydroxy-3-methylbutyloxy)-9,10-seco-5,7,10(19)-pregnatriene (22-oxa-1α,25-dihydroxyvitamin $D_3$; herein also referred to as maxacalcitol) have been reported to have epidermal cell growth-inhibiting and differentiation-inducing effects and to be useful as antipsoriatics (JPA Nos. 267550/86 and 183534/88). In development of dosage forms of antisporiatics, preparations for topical application are thought to be preferable because the target site of antipsoriatic therapy is epidermal cells.

However, no formulation for topical application containing maxacalcitol as an active ingredient and having excellent performance has been reported to date.

DISCLOSURE OF THE INVENTION

Preparations for topical application may be presented in such dosage forms as ointments, creams or lotions. Dosage forms vary with the application site. Ointments are applied over the whole body, especially under clothing. Creams are applied on parts exposed to the air such as the face or the hands, and lotions are applided to the scalp or the like. Especially, creams which are exposed to the air are required to have benefits such as non-tackiness after application and inconspicuous appearance at the treated site.

In the development of creams as one dosage form for topical application, O/W type creams containing a large amount of water in an outer water phase are thought to be most advantageous for seeking such benefits as non-tackiness after application and inconspicuous appearance at the treated site. O/W type creams containing maxacalcitol as an active ingredient may include two types, depending on whether the active ingredient exists in the oil phase or the water phase.

Maxacalcitol is known to be slightly soluble in water and to be unstable in aqueous solutions; it is also known to be highly soluble and have dramatically improved stability in organic solvents such as ethanol and chloroform and also to have very high stability in base materials such as petrolatum. Therefore, O/W type creams containing maxacalcitol in an inner oil phase have been supposed to be preferable for maintaining an advantageous creamy form and for stably containing the active ingredient maxacalcitol.

However, it is also important in development of creams to ensure chemical stability of the active ingredient, as well as physical stability of the emulsion. It is regarded that the physical stability of the emulsion depends on the concentrations of surfactants and co-surfactants; as both concentrations become higher and as the ratio of the concentrations becomes closer to a proper value, more stable emulsification is achieved.

As for the skin absorption of the active ingredient, the following are regarded as contributing to low skin absorption of the active ingredient:

1) high affinity of maxacalcitol for the oil phase base material, 2) low delivery or access rate of oil phase to skin, and 3) inhibition release of the maxacalcitol from the oil phase during transfer of maxacalcitol to skin. More specifically, transfer of maxacalcitol to skin may be inhibited by the presence of surfactants and co-surfactants at the oil/water interface or the presence of crystalline structures around oil-phase particles. Namely, when a drug is contained in the inner oil phase, the surfactant phase existing at the oil/water interface or the crystalline structures existing around the oil-phase particles during the release process may further hinder the release of the drug.

In order to eliminate the above disadvantages and enhance skin transfer by removing rate-limiting factors during the release process, we tried to develop a cream containing the drug maxacalcitol in the outer water phase and concurrently a cream containing maxacalcitol in the oil phase.

As described above, an object of the present invention is to provide a cream maintaining a creamy form, showing high skin absorption of the active ingredient maxacalcitol and stably maintaining said active ingredient for a long time-period.

As a result of careful studies conducted to find a cream showing high skin absorption of the active ingredient maxacalcitol and stably maintaining said active ingredient for a long time-period, we obtained the following finding. In O/W type creams wherein maxacalcitol exists in the oil phase, stability of the emulsion dramatically improved, however the skin transfer rate of the active ingredient decreased when the concentrations of surfactants and co-surfactants increased. In order to increase the skin transfer rate, it seemed necessary to decrease those factors which are regarded to be responsible for the absorption inhibition, in other words, the amount of surfactants existing at the oil/water interface or the amount of crystalline structures produced around oil-phase particles. Thus, we attempted to decrease the loading of surfactants and co-surfactants in so far as a stable emulsion would be maintained. As a result, we found that an excellent cream is provided when the total concentration of surfactants and co-surfactants in the cream is within the range of from 2 to 7% by weight. We also found that absorption can be controlled by incorporation of maxacalcitol in the oil phase, whereby an optimal level in skin can be maintained. A part of the present invention was accomplished on the basis of these findings.

As a result of careful studies to improve the skin absorption and the storage stability of creams containing maxacalcitol in the water phase, we also found that a homogeneous dispersion of maxacalcitol in the outer water phase ensures the storage stability of maxacalcitol and also remarkably improves the skin absorption to approximately twice as compared with creams containing maxacalcitol in the inner oil phase. A part of the present invention was accomplished on the basis of these findings.

As described above, we accomplished the present invention on the basis of the findings that incorporating maxacalcitol in the water phase can remarkably improve absorption and that incorporating maxacacitol in the oil phase can control absorption.

Moreover, we also found that the maxacalcitol level in skin can be controlled over a wide range, from low to high levels, by incorporation of maxacalcitol in both of oil and water phases.

Accordingly, the present invention provides an O/W type cream containing maxacalcitol in the oil phase and/or water phase.

According to an aspect of the present invention, there is provided an O/W type cream containing maxacalcitol and an emulsifier, wherein maxacalcitol exists in the oil phase.

In creams of the present invention, the emulsifier is preferably a mixture of a surfactant and a co-surfactant.

In creams of the present invention, the ratio between surfactants and co-surfactants is preferably within the range of from 1:1 to 1:11.

In creams of the present invention, the total concentration of surfactants and co-surfactants in a cream is preferably within the range of from 2 to 7% by weight.

In creams of the present invention, the surfactant is preferably an ether-type surfactant.

In creams of the present invention, the surfactant is more preferably a polyoxyethylene alkyl ether.

In creams of the present invention, the co-surfactant is preferably a higher alcohol.

In creams of the present invention, the co-surfactant is more preferably stearyl alcohol, cetyl alcohol or cetostearyl alcohol.

In creams of the present invention, the ratio of oil phase in an O/W type cream is preferably within the range of from 30 to 50% by weight.

According to another aspect of the present invention, there is provided an O/W type cream, wherein maxacalcitol exists in the water phase.

According to an embodiment of the O/W type cream wherein maxacacitol exists in the water phase, there is provided an O/W cream wherein crystalline maxacalcitol is pulverized and contained in the water phase.

According to another embodiment of the O/W type cream wherein maxacalcitol exists in the water phase, there is provided an O/W cream wherein crystalline maxacalcitol is dissolved in an organic solvent and contained in the water phase.

According to still another embodiment of the O/W type cream wherein maxacalcitol exists in the water phase, there is provided an O/W cream containing an alcohol and/or a nonionic surfactant in the water phase.

BRIEF DESCRIPTION OF THE DRAWING

FIG. 1 is a graph showing the relationship between the concentration of cetostearyl alcohol and skin transfer rate of creams of the present invention wherein maxacalcitol exists in the oil phase.

PREFERRED EMBODIMENTS OF THE INVENTION

The present invention relates to O/W type creams wherein maxacalcitol exists in the oil phase and/or water phase.

$1\alpha,3\beta$-Dihydroxy-$20\alpha$-(3-hydroxy-3-methylbutyloxy)-9, 10-seco-5,7,10(19)-pregnatriene (22-oxa-$1\alpha,25$-dihydroxyvitamin $D_3$; herein also referred to as maxacalcitol) contained in cream of the present invention as an active ingredient is a known vitamin $D_3$ derivative and can be synthesized by the process described in JP No. 267550/86, for example.

The amount of maxacalcitol contained in creams of the present invention is a therapeutically effective amount for the skin disease to be treated, normally within the range of from about 1 $\mu$g/g to about 200 $\mu$g/g, preferably about 2 $\mu$g/g to about 100 $\mu$g/g.

Creams of the present invention include three embodiments wherein maxacalcitol exists in the oil phase, water phase or both. The first two embodiments wherein maxacalcitol exists in the oil phase or the water phase are specifically described below, but it should be understood that the following description is also applicable to the case where maxacalcitol exists in both oil and water phases.

(1) Maxacalcitol Exists in the Oil Phase:

Surfactants suitable for creams of the present invention preferably include ether-type surfactants, especially polyoxyethylene alkyl ethers such as Cetomacrogol™ 1000. Surfactants are desirably added to both of the inner oil phase and the outer water phase so as to prepare a stable emulsion.

Co-surfactants suitable for creams of the present invention preferably include higher alcohols, especially stearyl alcohol, cetyl alcohol or a mixture of both, i.e. cetostearly alcohol.

In order to maintain stability of the emulsion and enhance the skin transfer rate of the active ingredient, the total concentration of surfactants and co-surfactants is preferably within the range of from 2 to 7% by weight. A stable emulsion was obtained when the ratio between surfactants and co-surfactants was within the range of from 1:1 to 1:11, more preferably 1:4.

Base materials for the oil phase of O/W creams include petrolatum, liquid paraffin, wax or the like. During addition of maxacalcitol to the oil phase, it is convenient to use a solubilizer or solvent promoter suitable for facilitating dissolution of maxacalcitol. Oil phase can be prepared by, for example, first dissolving maxacalcitol in a solvent promoter such as ethanol, then adding the solution to a solubilizer such as middle chain fatty acid triglyceride (MCT) and finally adding the resulting mixture to a base material such as petrolatum as mentioned above.

Suitable solubilizers other than middle chain fatty acid triglyceride (MCT) include isopropyl myristate, diisopropyl adipate, and triacetin.

The water phase of O/W type creams may optionally contain surfactants and can be adjusted to a desired pH with an appropriate butter (PBS or the like).

Oil and water phase may appropriately contain preservatives (such as methylparaben) or the like.

(2) Maxacalcitol exists in the water phase

Maxacalcitol can be effectively dispersed in the outer water phase either by homogeneously dispersing a maxacalcitol stock pulverized by a jet mill or the like or dissolving maxacalcitol in an organic solvent such as ethanol and then homogeneously dispersing the solution in the outer water phase.

Maxacalcitol is not stable in aqueous solutions and therefore simply dispersing it after pulverization or simply dispersing it as a solution in ethanol or the like is sometimes insufficient to maintain its heat stability. Thus, an alcohol and/or a nonionic surfactant may be assed to the outer water phase for the purpose of improving heat stability of maxacalcitol. As a result, not only heat stability but also skin transfer of maxacalcitol can be controlled.

Alcohols that can be added to the outer water phase include monohydric alcohols or dihydric alcohols. Preferred monohydric alcohols include ethanol, and preferred dihydric alcohols include glycols, among which propylene glycol and 1,3-butylene glycol are especially preferred.

Nonionic surfactants that can be added to the outer water phase preferably include ether-type surfactants, especially polyoxyethylene alkyl ethers and Pluronic™-type surfactants. Specific examples of nonionic surfactants include Cetomacrogol 1000.

When maxacalcitol is contained as an active ingredient in the water phase of O/W type creams of the present invention, the water phase can be adjusted to a desired pH using an appropriate buffer (such as PBS).

Base materials for the oil phase of O/W type creams include Petrolatum, liquid paraffin and wax.

Oil and water phases may further contains surfactants and/or co-surfactants for the purpose of obtaining a stable emulsion.

Examples of surfactants existing in the oil phase preferably include ether-type surfactants, particularly polyoxyethylene alkyl ethers such as Cetomacrogol 1000.

Examples of co-surfactants existing in the oil phase preferably include higher alcohols, especially stearyl alcohol, cetyl alcohol or a mixture of both, i.e. cetostearyl alcohol.

The total concentration of surfactants and co-surfactants is not specifically limited in the present invention and can be appropriately controlled, but typically within the range of from 2 to 7% by weight. The ratio between surfactants and co-surfactants is not specifically limited either in the present invention, but typically within the range of from 1:1 to 1:11, preferably 1:4.

The oil and water phases may appropriately contain preservatives (such as methylparaben) or the like.

The proportion of the oil phase in O/W type creams (wherein maxacalcitol exists in the oil or water phase) can be appropriately selected, but preferably 30–50% by weight, most preferably about 40% by weight.

Creams of the present invention can be used to treat various cases of psoriasis such as psoriasis vulgaris, psoriasis pustulosa, psoriasis guttata, erythroderma psoriaticum, psoriasis arthropathica and psoriasis gravis. The dose depends on the condition of the disease or other factors, but preferably a cream containing 2 µg/g to 100 µg/g of maxacalcitol is administered once to several times per day.

The following examples further illustrate the present invention without limiting the same thereto.

EXAMPLES

Preparation Example A-1

The oil phase components and water phase components shown in the following Formulation example A-1 were dissolved on an oil bath at 75° C.–80° C. The content of maxacalcitol in the whole cream was 50 µg/g, the concentration of cetostearyl alcohol was 7.2% by weight and the concentration of Cetomacrogol 1000 was 1.8% by weight.

| Formulation example A-1: | |
|---|---|
| | Amount |
| Oil phase components | |
| Maxacalcitol | 5.0 mg |
| Ethanol | 50 µl |
| MCT | 1.0 g |
| Cetostearyl alcohol | 7.2 g |

| -continued | |
|---|---|
| Formulation example A-1: | |
| | Amount |
| Cetomacrogol 1000 | 1.8 g |
| Methylparaben | 0.04 g |
| White Petrolatum | Adjusted to 40.0 g in total |
| Water phase components | |
| Cetomacrogol 1000 | 0.02 g |
| Methylparaben | 0.04 g |
| PBS (25 mM, pH 8.0) | Adjusted to 60.0 g in total |

The oil phase components and water phase components were mixed and stirred by a homomixer and a paddle mixer while the temperature was maintained at 75° C. to 80° C. The homomixer was stopped and the mixture was cooled with stirring by the paddle mixer to give the desired cream.

Preparation Example A-2

A cream was prepared by the same procedure as in Preparation example A-1 except that the concentrations of maxacalcitol, cetostearyl alcohol and Cetomacrogol 1000 were 50 µg/g, 5% by weight and 1.25% by weight, respectively.

Preparation Example A-3

A cream was prepared by the same procedure as in Preparation example A-1 except that the concentrations of maxacalcitol, cetostearyl alcohol and Cetomacrogol 1000 were 50 µg/g, 4% by weight and 1% by weight, respectively.

Preparation Example A-4

A cream was prepared by the same procedure as in Preparation example A-1 except that the concentrations of maxacalcitol, cetostearyl alcohol and Cetomacrogol 1000 were 50 µg/g 3% by weight and 0.75% by weight, respectively.

Test Example A-1 (Skin Absorption Test)

Each of the creams obtained in the above Preparation examples A-1 to A-5 was applied on the dorsal skin of 7-week old male SD rats and the rate of maxacalcitol left on the skin and the level of maxacalcitol in the skin were determined 4 hours after the application.

Rats were maintained at a constant temperature and a constant humidity with solid diet and water in vitae, and cervicodorsally shaved with an electric clipper and a shaver on the day before administration. On the test day, a 4×3 cm plastic frames was fixed on the shaved portion of the skin under ether anesthesia and 15 µg of maxacalcitol/0.3 g cream/kg was applied to exactly within that portion of the skin with a spatula or the like. After 4 hours, the cream was wiped off with 3 pieces of absorbent cotton soaked in 70% ethanol and assayed for the amount of maxacalcitol left on the skin. After completion of wiping, a 3×4 cm skin section was cut out from the treated site and assayed for the amount of maxacalcitol in the skin.

The results are shown in FIG. 1.

Test Example A-2 (Stability Test)

The creams of Preparation examples A2–A5 were evaluated for physical and chemical stability. Vials charged with the creams were accelerated in an incubator and samples over time. The resulting creams were observed with the naked eye to evaluate the emulsification state; the maxacalcitol content in the creams was measured to evaluate the rates of residual maxacalitol tot he initial amount.

The results are shown in Table 1.

TABLE 1

| | Preparation examples | | | |
|---|---|---|---|---|
| | A-5 | A-4 | A-3 | A-2 |
| Cetostearyl alcohol | 2% | 3% | 4% | 5% |
| Initial (%) | 100 | 100 | 100 | 100 |
| 80° C., 1 week (%) | 83.21# | 83.11# | 84.47# | 82.94# |
| 80° C., 2 weeks (%) | 60.44# | 60.63# | 69.76# | 63.82# |
| 80° C., 3 weeks (%) | 44.94# | 46.36# | 54.51# | 40.99# |
| 60° C., 2 weeks (%) | 96.27# | 94.83# | 94.88# | 91.98# |
| 60° C., 4 weeks (%) | 94.06# | 93.66# | 94.78# | 91.76# |
| 60° C., 3 months (%) | 73.21# | 79.40# | 81.59# | 75.22# |
| 50° C., 2 weeks (%) | # | 99.61# | 99.22# | # |
| 50° C., 4 weeks (%) | 96.38# | 101.53# | 100.77# | 95.67# |
| 40° C., 4 weeks (%) | 97.14# | 98.99 | 98.90 | 95.77 |
| 40° C., 3 months (%) | 95.13# | 96.21 | 96.64 | 97.32 |

Phase separation occurred.

Desirable creams should have high skin absorption, high drug utilization and high storage stability. As an initial stage, a formulation similar to existing commercially available creams was employed (Preparation example A-1), revealing such low skin-absorption that further improvement in adsorption seemed necessary. The low absorption was believed to be attributable to 1) high affinity of maxacalcitol for the oil phase base material, 2) low delivery or probability of access of the oil phase to skin, and 3) inhibition of release of the maxacalitol from the oil phase during maxacalitol transfer to skin, so that the formulation was modified to be improved in these factors.

As measured to deal with these factors 1), 2) and 3), we decided to decrease the amount of the cosolubilizer MCT, increase the proportion of oil phase and decrease the surfactant concentration at the oil/water interface and around oil phase particles, respectively. In order to maintain an emulsion form in O/W type creams, at least 2% of cetostearyl alcohol was required in a preparation and the most preferred concentration of Cetomacrogol 1000 in that case was 0.5%, which corresponds to ¼ of the concentration of cetostearyl alcohol (preparation example A-5; all the emulsifier concentrations mentioned hereinbelow are the concentrations of cetostearyl alcohol and the concentrations of Cetomacrogol 1000 are ¼ of those concentrations unless otherwise specified).

A cream having the lowest possible emulsifier concentration in so far as an emulsion could be maintained was evaluated for skin absorption and physical and chemical stability (FIG. 1 and Table 1). In the cream having a decreased emulsifier concentration, skin absorption was improved, however phase separation occurred at week 2 at 40° C. which evidenced low physical stability. Under microscopic observation, oil phase particles of this cream had larger diameters and wider particle-size-distribution as compared with those in creams having high emulsification stability; also observed were fine particle masses which were presumably petrolatum; these data indicated that the emulsifier concentration was too low to achieve complete emulsification.

Considering that establishing a stable emulsion by increasing the emulsifier is essential to ensure high physical stability, we selected creams having emulsifier concentrations which were increased to 3%-5% (Preparation examples A-2 to A-4) and evaluated them for skin absorption and physical and chemical stability (FIG. 1 and Table 1). Formulations having cetostearyl alcohol concentrations of 3% to 5% showed higher skin transfer rates than that of the initial formulation. However, the skin transfer rates were comparable and independent of the emulsifier concentration in the tested range. As is apparent from Table 1, these formulations did now show the phase separation in the early stage, which phase separation had occurred at the cetostearyl alcohol concentration of 2%; their improved physical stability was apparent. As to chemical stability, the creams with cetostearyl alcohol concentrations of 3% or more showed high residual rates of maxacalcitol at cetostearyl alcohol concentrations of 3% to 5%, suggesting that they all can be stored at room temperature; in fact the cream with a cetostearyl alcohol concentration of 4% was considered to be most preferable because it was most stable at higher temperature.

Preparation Example B-1

The oil phase components and the water phase components (except for maxacalcitol) that are shown in the following Formulation example B-1 were dissolved in an oil bath at 75° C. to 80° C. The concentration of cetostearyl alcohol in this case was 4.0% by weight and the concentration of Cetomacrogol 1000 was 1.0 by weight. The two phase components were mixed and stirred by a homomixer and a paddle mixer while the temperature was maintained at 75° C. to 80° C. The homomixer was stopped and the mixture was cooled with stirring by the paddle mixer to give a cream. The resulting cream was combined with a solution of maxacalcitol in ethanol and the mixture was stirred to homogeneity.

Formulation example B-1:

| Oil Phase | |
|---|---|
| MCT (middle chain fatty acid triglyceride) | 1.0 g |
| Cetostearyl alcohol | 4.0 g |
| Cetomacrogol 1000 | 1.0 g |
| Methylparaben | 0.04 g |
| White petrolatum | Adjusted to 40.0 g in total |
| Water phase | |
| Cetomacrogol | 0.02 g |
| Methylparaben | 0.04 g |
| PBS (25 mM, pH 8.0) | to 60.0 g |
| Maxacalcitol | 5.0 mg |
| Ethanol | 50 μ |

Comparison Example B-1

For comparison, oil phase components and water phase components shown in the following Comparison formulation example B-1 were dissolved on an oil bath at 75° C. to 80° C. in this Comparison formulation example B-1, the active ingredient maxacalcitol exists in the oil phase. The oil and water phases were mixed and stirred by a homomixer and a paddle mixer while the temperature was maintained at 75° C. to 80° C. The homomixer was stopped and the mixture was cooled with stirring by the paddle mixer to give a cream.

Comparison formulation example B-1 (Comparison example)

| Oil phase | |
|---|---|
| Maxacalcitol/Ethanol | 5.0 mg/50 µl |
| MCT (middle chain fatty acid triglyceride) | 1.0 g |
| Cetostearyl alcohol | 4.0 g |
| Cetomacrogol 1000 | 1.0 g |
| Methylparaben | 0.04 g |
| White petrolatum | Adjusted to 40.0 g in total |
| Water phase | |
| Cetomacrogol 1000 | 0.02 g |
| Methylparaben | 0.04 g |
| PBS (25 mM, pH 8.0) | Adjusted to 60.0 g in total |

Text Example B-1

The creams obtained in the above Preparation example B-1 and Comparison example B-1 were evaluated for skin transfer, physical stability and chemical stability.

For evaluation of skin transfer, rats were maintained at a constant temperature and a constant humidity with solid diet and water in vitae, and cervicodorsally shaved with an electric clipper and a shaver on the day before administration. On the test day, 1 4×3 cm plastic frame was fixed on the shaved portion of the skin under ether anesthesia and 15 µg of maxacalcitol/0.3 g cream/kg was applied to exactly within that portion of the skin with a spatula or the like. After 4 hours, the applied cream was wiped off with 3 pieces of absorbent cotton soaked in 70% ethanol and assayed for the amount of maxacalcitol left on the skin.

For evaluation of stability, vials charged with the creams were maintained in an incubator and sampled at predetermined times. The resulting creams were observed with the naked eye to evaluate the emulsification state; the maxacalcitol content in the creams was measured to evaluate the rates of residual maxacalcitol to the initial amount.

The results are shown in Table 2.

TABLE 2

| | Formulation example B-1 | Comparison formulation example B-1 |
|---|---|---|
| Unabsorbed rate after 4 hours | 62.1% (n = 3) | 81.9% (n = 7) |
| Storage stability | 95.6 (25° C., 6 months) | 96.6% (40° C., 3 months) |

As compared with the cream containing maxacalcitol in the inner oil phase (Comparison formulation example B-1), the cream having the same formulation but containing maxacalcitol in the outer water phase showed excellent improvement in skin transfer rate, which doubled to approximately 40% in 4 hours as shown in Table 2. It also showed high storage stability of 95.6% at 25° C. after 6 months, but further improvement was desired.

Preparation Example B-2

The oil phase components and the water phase components (except for maxacalcitol) that are shown in the following Formulation example B-2 were dissolved in an oil bath at 75° C. to 80° C. The concentration of cetostearyl alcohol was 4.0% by weight and the concentration of Cetomacrogol 1000 was 1.0% by weight. The two phase components were mixed and stirred by a homomixer and a paddle mixer while the temperature was maintained at 75° C. to 80° C. The homomixer was stopped and the mixture was cooled with stirring by the paddle mixer to give a cream. The resulting cream was combined with a solution of maxacalcitol in ethanol and the mixture was stirred to homogeneity.

Maxacalcitol is known to be unstable in aqueous solutions. The cream of Preparation example B-1 is also somewhat defective in chemical stability. However, as shown in Formulation example B-2, by adding alcohols or glycols to the water phase, the chemical stability can be dramatically improved, for example, by a factor of several dozens without affecting skin transfer rate. These properties can be controlled by changing the proportions of glycols.

Formulation example B-2:

| Oil phase | |
|---|---|
| MCT (middle chain fatty acid triglyceride) | 1.0 g |
| Cetostearyl alcohol | 4.0 g |
| Cetomacrogol 1000 | 1.0 g |
| Methylparaben | 0.04 g |
| White petrolatum | Adjusted to 40.0 g in total |
| Water phase | |
| Cetomacrogol 1000 | 0.02 g |
| Methylparaben | 0.04 g |
| Propylene glycol | 30.0 g |
| Butylene glycol | 12.0 g |
| PBS (25 mM, pH 8.0) | To 60.0 g |
| Maxacalcitol | 5.0 mg |
| Ethanol | 50 µl |

Industrial Applicability

In O/W type creams of the present invention, high physical and chemical stability and improved skin transfer rate of maxacalcitol were achieved by modifying the elulsifier concentration, oil/water ratio or the like in the formulations or by suitably incorporating maxacalcitol in the water phase. According to the present invention, therefore, excellent preparations showing improved skin transfer and heat stability of the active ingredient can be simultaneously developed.

What is claimed is:

1. An O/W cream comprising maxicalcitol as an active ingredient, wherein the maxacalcitol is present in the water phase, and the cream comprising from 2 to 7% by weight of a mixture of a surfactant and a cosurfactant.

2. The cream according to claim 1 wherein the ratio between the surfactant and the cosurfactant is within the range of from 1:1 to 1:11.

3. The cream according to claim 1 wherein the surfactant is an ether surfactant.

4. The cream according to claim 3 wherein the surfactant is a polyoxyethylene alkyl ether.

5. The cream according to claim 1 wherein the cosurfactant is a higher alcohol.

6. The cream according to claim 1 wherein the cosurfactant is stearyl alcohol, cetyl alcohol, or cetostearyl alcohol.

7. The cream according to claim 1 wherein the proportion of the oil phase in the O/W cream is within the range of from 30% by weight to 50% by weight.

* * * * *